United States Patent
Krebs et al.

(10) Patent No.: US 9,127,301 B2
(45) Date of Patent: Sep. 8, 2015

(54) METHOD OF DETECTING THE PRESENCE OF POLYCYCLIC AROMATIC HYDROCARBONS

(71) Applicants: Joseph F. Krebs, Austin, TX (US); John Duvall-Jisha, Austin, TX (US); Sol Resnick, Austin, TX (US)

(72) Inventors: Joseph F. Krebs, Austin, TX (US); John Duvall-Jisha, Austin, TX (US); Sol Resnick, Austin, TX (US)

(73) Assignee: BIOO SCIENTIFIC CORPORATION, Austin, TX (US)

( * ) Notice: Subject to any disclaimer, the term of this patent is extended or adjusted under 35 U.S.C. 154(b) by 0 days.

(21) Appl. No.: 14/086,396

(22) Filed: Nov. 21, 2013

(65) Prior Publication Data

US 2014/0154723 A1    Jun. 5, 2014

Related U.S. Application Data

(60) Provisional application No. 61/729,035, filed on Nov. 21, 2012.

(51) Int. Cl.
*C12Q 1/26* (2006.01)
*C12N 9/02* (2006.01)
*G01N 33/52* (2006.01)

(52) U.S. Cl.
CPC .............. *C12Q 1/26* (2013.01); *C12N 9/0071* (2013.01); *G01N 33/52* (2013.01)

(58) Field of Classification Search
USPC ............................................ 435/25, 26, 262.5
See application file for complete search history.

(56) References Cited

U.S. PATENT DOCUMENTS 6,794,167 B2 *    9/2004    Parales et al. ................. 435/189

OTHER PUBLICATIONS

Jouanneau Y. et al. Characterization of a Naphthalene Dioxygenase . . . Biochemistry 45(40)12380-91, 2006.*
Eaton, R. et al., Bacterial Metabolism of Naphthalene: Construction and Use of Recombinant Bacteria to Study Ring Cleavage of 1,2—Dihydroxynaphthalene and Subsequent Reactions; J of Bacteriology, vol. 174, No. 23, 1992, pp. 7542-7554.

* cited by examiner

*Primary Examiner* — Ralph Gitomer

(57) ABSTRACT

Described herein is a rapid coupled enzymatic assay to detect polycyclic aromatic hydrocarbon (PAH) compounds in samples. The method uses a detection composition that includes: a buffered solution comprising NADH; naphthalene dioxygenase, naphthalene 1,2-dihydroxy-1,2-dihydronaphthalene dehydrogenase, and 1,2-dihydroxynaphthalene dioxygenase. The presence of PAH is determined by noting a color change of the detection composition, either visually or spectrophotometrically.

10 Claims, 5 Drawing Sheets dioxygenase holoenzyme

METHOD OF DETECTING THE PRESENCE OF POLYCYCLIC AROMATIC HYDROCARBONS

PRIORITY CLAIM

This application claims the benefit of U.S. Provisional Application No. 61/729,035 filed on Nov. 21, 2012.

BACKGROUND OF THE INVENTION

1. Field of the Invention

The present invention generally relates to the detection of hydrocarbons in food. More particularly the invention relates to the detection of polyaromatic hydrocarbons in food and environmental samples.

2. Description of the Relevant Art

Oil spills are a source of ecological devastation which poses major threats to the environment and human health. Spilled petroleum can rapidly spread through the sea to contaminate large marine areas. This is especially true for larger oil spills produced by offshore drilling or transportation. Once released into the marine environment, the hydrophobic and persistent characteristics of petroleum create a lingering threat to aquatic life and seafood over vast areas. The persistent, bioaccumulative nature of petroleum causes the extended presence of petroleum constituents in aquatic organisms (including seafood) long after the oil has dissipated from the sea water. Spilled petroleum constituents accumulate in sediments as well as are directly ingested and absorbed by many species of marine life, especially shellfish, where they accumulate over time. Many species of seafood, such as mollusks and crustaceans, do not efficiently metabolize petroleum components which accumulate in their tissues. Consequently, recovery of seafood stocks from large-scale oil spills to baseline hydrocarbon levels can take years.

Petroleum is comprised of a number of components which pose human health concerns, such as alkanes, monoaromatic hydrocarbons, and polycyclic aromatic hydrocarbons (PAHs). PAHs. Exemplary polyaromatic hydrocarbons are depicted in FIG. 1. PAHs are especially troublesome contaminants to deal with after an oil spill, compared to other petroleum components because: i) PAHs have relatively high molecular weights and boiling points so, unlike most alkanes and monoaromatic compounds in petroleum, they are not "weathered" out of the marine environment by atmospheric contact (causing them to remain in the environment over time); ii) they are slowly metabolized in animals; and iii) PAHs can be very toxic and carcinogenic. Toxicology studies indicate that, when ingested, PAHS (such as benzo(a)pyrene and naphthalene) can cause adverse health effects in humans such as cancer, liver damage, birth defects, and testicular toxicity. Some PAH compounds, such as benzo(a)pyrene, are converted to an epoxide form in the liver which can react with DNA to form covalent adducts. These adducts can cause genetic mutations in vivo, especially in the liver. For these reasons petroleum-adulterated seafood cannot be sold in the U.S. Additionally, seafood cannot be harvested from areas affected by oil spills. For example, large fishery areas of the Gulf of Mexico were closed by NOAA because of the Deepwater Horizon/BP oil spill (FDA letter; Jun. 14, 2010). There is now an especially strong need to monitor petroleum constituent levels in seafood in affected areas.

After an oil spill, it is critical to perform quality, high capacity petroleum tests for seafood samples for two reasons: Testing ensures that adulterated seafood does not reach consumers. Additionally, testing provides analysts with valuable information to determine when affected areas have to be closed and, eventually, reopened when samples have returned to baseline levels of petroleum constituents. Currently PAH contamination in seafood is measured using three approved methods: gas chromatography mass spectrometry (GCMS), high performance liquid chromatography (HPLC), and sensory testing (organoleptic "taint" test).

While GCMS is a powerful analytical method, it requires expensive instrumentation, highly-skilled operators, extensive sample prep and it takes considerable time to perform (samples are tested one at a time). While HPLC methods require less sample prep than GCMS, they also require expensive instruments and highly skilled operators. Both GC/MS and HPLC methods require use of toxic organic solvents. GCMS and HPLC methods have limited throughput capacity. In practice, human sensory (organoleptic) testing is now used as an initial primary screen for seafood petroleum adulteration. However, organoleptic methods have their own disadvantages because: i) they are somewhat subjective; ii) they do not provide quantitative data; and iii) they are less accurate and sensitive than GCMS and HPLC, especially for the detection of larger, more carcinogenic PAH compounds. For example, recent comparisons by NOAA of the GCMS and sensory methods using seafood samples from environmental spills indicates that, while sensory testing sometimes agrees well with GCMS results, in a number of cases, samples of whiting, North Cape "finfish", clams, oyster and mussel containing potentially dangerous levels of PAH compounds (1-24 ppm) did not exhibit any discernible taint. Organoleptic testing also requires skilled, seven member teams in an environmentally-controlled environment. These issues have caused some scientists and seafood producers to question the accuracy and effectiveness of sensory testing.

Immunological methods use antibodies which lack sufficient specificity and robustness for routine, reliable detection of PAH compounds in seafood samples. To increase the accuracy and efficiency of testing, it would be highly desirable to develop new high-throughput, high quality tests for petroleum components in food and environmental samples.

SUMMARY OF THE INVENTION

The disclosure describes a rapid method and test kit to detect polycyclic aromatic hydrocarbons (PAHs) in samples. PAH compounds are primary constituents of petroleum and can be used as markers to detect petroleum contamination. The disclosed method uses a coupled enzymatic reaction to first oxidize PAH compounds to diols and then cleave the diols to form visibly colored products. The stabilized assay formulation allows the use of partially purified dioxygenase enzymes for the reaction, thereby preventing the loss of activity normally observed for these enzymes. The broad substrate specificity of the coupled reaction enables detection of a wide range of PAH compounds. This assay can be performed on a variety of food and environmental samples. The robust nature of the enzymatic detection reaction permits the use of simple, streamlined sample preparation methods. The cumulative color production generated from the complex ensemble of PAH compounds found in petroleum can create an intense signal and make the method well-suited to detect petroleum contamination. The cleavage products can be visually detected or detected using a spectrophotometer or plate reader.

In an embodiment, a method of detecting polycyclic aromatic hydrocarbons includes: adding a sample suspected of containing one or more polycyclic aromatic hydrocarbons to a detection composition, wherein the detection composition comprises: NADH; naphthalene dioxygenase; naphthalene 1,2-dihydroxy-1,2-dihydronaphthalene dehydrogenase; and 1,2-dihydroxynaphthalene dioxygenase; and determining if the color of the detection composition has changed due to the presence of polycyclic aromatic hydrocarbons. The sample may be derived from a food source or an environmental source.

In an embodiment, the naphthalene dioxygenase is stabilized naphthalene dioxygenase. Stabilized naphthalene dioxygenase is produced by the method including: obtaining naphthalene dioxygenase from a bacterial source; and dialyzing the obtained naphthalene dioxygenase using dialysis tubing having a molecular weight cut off (MWCO) of less than or equal to about 7500. In some embodiment, the dialysis is performed in the presence of dithiothreitol (DTT) and/or glycerol.

In an embodiment, the naphthalene 1,2-dihydroxy-1,2-dihydronaphthalene dehydrogenase and the 1,2-dihydroxynaphthalene dioxygenase are desalted before use in the detection composition.

The change in the color of the detection composition may be determined visually or spectrophotometrically. In an embodiment, the change in the color of the detection composition is determined by detecting a change in the specific absorbance of ultraviolet or visible light by the detection composition. In an embodiment, the change in the color of the detection composition is determined by detecting a change in the specific absorbance at wavelengths of between about 360 nm to about 550 nm.

In an embodiment, a method of producing stabilized naphthalene dioxygenase includes: obtaining a naphthalene dioxygenase fraction from lysed cells of a bacterial strain which can produce all four subunits of naphthalene dioxygenase; dialyzing the obtained naphthalene dioxygenase using dialysis tubing having a molecular weight cut off (MWCO) of less than or equal to about 7500. The bacterial strain may be *Pseudomonas putida* or the naphthalene dioxygenase can be produced recombinantly in active form from *E. coli*.

In an embodiment, obtaining the naphthalene dioxygenase fraction includes: growing the a bacterial strain which can produce all four subunits of naphthalene dioxygenase; separating the grown cells from the growth medium; lysing the separated cells; and separating the naphthalene dioxygenase fraction from the insoluble fraction of the lysed separated cells. To improve stability of the naphthalene dioxygenase, the naphthalene dioxygenase fraction obtained from the lysed separated cells is subjected to dialysis prior to any substantial storage or freezing of the naphthalene dioxygenase fraction.

Dialysis of naphthalene dioxygenase is performed in the presence of dithiothreitol (DTT) and/or glycerol. In some embodiment, dialysis is performed in a buffered solution having a pH of about 8, at a temperature of less than 25° C.

In an embodiment, a test kit to detect polycyclic aromatic hydrocarbons in a sample includes: a buffered solution comprising NADH; naphthalene dioxygenase, naphthalene 1,2-dihydroxy-1,2-dihydronaphthalene dehydrogenase, and 1,2-dihydroxynaphthalene dioxygenase.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
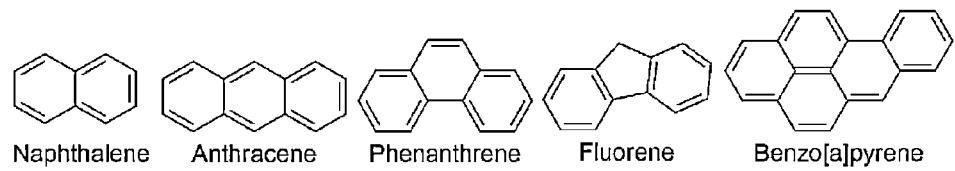
FIG. 1 depicts chemical structures of representative polycyclic aromatic (PAH) compounds.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Enzyme-based assays are powerful tools for analytical testing. Enzymatic tests have long been used for a wide variety of clinical testing applications including detecting DNA mutations, post-translational protein modifications and measuring serum components such as glucose, triglycerides and proteins. Enzyme tests are also commercially used in various food testing applications such as toxin detection, vitamin/nutrient analysis, and confirmation of successful milk pasteurization. Enzymatic tests provide several important advantages for analyte detection over other analytical methods: they are typically rapid, specific, homogeneous and direct. Unlike conventional HPLC or GCMS methods, enzyme assays do not require expensive instruments, equipment or skilled operators. Also, unlike HPLC and GCMS techniques, enzyme assays are compatible with detergents. In contrast to immunological methods such as ELISA, enzyme assays do not require time-consuming laborious incubation and wash steps.

The microbial world provides us with an immense natural library of enzymes for the development of new analytical tests. Microbial enzymes possess physical properties which make them ideal reagents from a commercial perspective. Microbial enzymes are highly specific and efficient—capable of binding and transforming specific substances even in crude mixtures (such as food samples). They are often very stable and can withstand higher temperatures, chaotropes and organic solvents.

Figure 2:
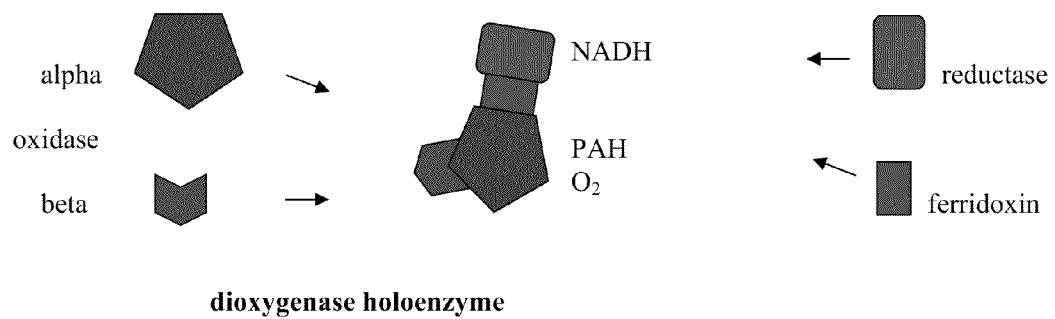
FIG. 2 depicts schematic diagrams of the subunit composition and assembly of microbial PAH dioxygenases.

Microbial PAH dioxygenase enzymes are an interesting class of enzymes which evolved to degrade/metabolize polyaromatic hydrocarbons (PAHs) in the environment. They have recently been characterized at the genetic and biochemical level. Microbial dioxygenases are generally comprised of three distinct components: a reductase component which binds and oxidizes NADH, an oxidase component which binds both the PAH and molecular oxygen ($O_2$), and a ferridoxin component which shuttles electrons between reductase and oxidase (see FIG. 2). In bacteria such as *Pseudomonas putida*, these enzymes are used to metabolize PAH compounds as a carbon source for growth (in conjugation with other downstream metabolic enzymes such as naphthalene 1,2-dihydroxy-1,2-dihydronaphthalene dehydrogenase and 1,2-dihydroxynaphthalene dioxygenase).

The oxidase component is often comprised of two distinct protein subunits: a larger alpha subunit containing the catalytic domain and a beta subunit which stabilizes the alpha subunit structure. Dioxygenases which degrade PAH compounds have been expressed in *E. coli*, but are very hard to purify in an active form. While these enzymes are, in principle, well-suited for industrial applications such as environmental bioremediation after an oil spill, their multisubunit structure can be rather unstable which limits their commercial utility. Consequently, PAH dioxygenase enzymes have never been used for detection of PAH compounds. The inherent instability of PAH dioxygenase enzymes makes them very difficult to purify and use for commercial purposes.

This disclosure relates to a method that uses microbial enzymes which degrade polyaromatic hydrocarbons to detect polycyclic aromatic hydrocarbons (PAH) in food and environmental samples. The first step in PAH degradation uses a PAH dioxygenase (PAHDO) enzyme such as naphthalene 1,2-dioxygenase (NDO) or biphenyl dioxygenase (BDO) to convert the PAH compound to PAH-(cis)-diol in an NADH- or NADPH-dependent manner.

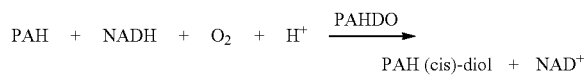

Next the PAH diol is subsequently reduced and oxidized in two successive reactions to produce a colored "chromene" product. The first reaction is catalyzed by the 1,2-dihydroxy-1,2-dihydronaphthalene dehydrogenase enzyme (NahB), while the second reaction is catalyzed by the enzyme 1,2-dihydroxynaphthalene dioxygenase (NahC). These enzymes are both derived from the bacteria *Pseudomonas putida*.

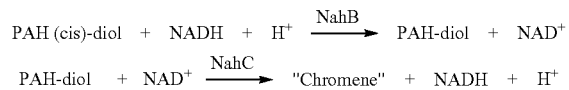

When these enzymes are used in succession, they function sequentially to convert colorless PAH compounds into a readily-detectable visible product class known as PAH chromene compounds.

The enzymes for the three reactions originate in the bacteria *Pseudomonas putida*. They all can be produced recombinantly in active form from *E. coli*. The naphthalene dioxygenase enzyme is a multisubunit enzyme containing two labile cofactors. To maximize assay sensitivity while preserving maximal enzymatic activity, the cell extracts must be carefully produced and stored to facilitate the correct association of the enzyme subunits as well as the reduced state of the iron-sulfur cofactor. The dialysis step is particularly important for the production of stable, highly active naphthalene dioxygenase. Dialysis pore size must be chosen carefully (≤7000 MWCO) in order to avoid the loss of the ferredoxin subunit. To improve stability, dialysis should be conducted directly after cell lysis, any storage or freezing between lysis and dialysis significantly reduces activity. The presence of dithiothreitol (DTT) and/or glycerol in the dialysis buffer also improves the stability and activity of the naphthalene dioxygenase enzyme.

Careful desalting of the NahB and NahC proteins must be performed to reduce reaction background signal while maintaining high levels of enzymatic activity. The NahB and NahC enzymes were found to be nearly intolerant of dialysis. However, partially-purifying the protein using PD-10 desalting columns into Tris buffer pH 8.5 not only increased activity for both NahB and NahC but preserved that activity over 3 freeze/thaw cycles. This desalting process also reduces the background absorbance of the assay which allows increased assay sensitivity.

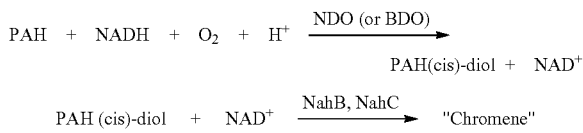

This coupled reaction is useful for the detection of polyaromatic hydrocarbons in a number of food and environmental samples including but not limited to finfish, clams, crabs and water samples. The robust nature of the enzymatic reactions permits the use of simple, streamlined sample preparation methods prior to the enzymatic reaction. The colorimetric assay has a broad versatility for the PAH detection since it has been used to detect a wide variety of PAH compounds such as naphthalene, biphenyl, carbazole, anthracene, phenanthrene, fluorene, and benz(a)pyrene. Since polyaromatic compounds such as these are commonly-used markers for petroleum, this reaction is useful for the rapid, colorimetric detection of petroleum contamination in food and environmental samples.

To provide rapid qualitative detection of PAH compounds, the assay can be used without an instrument (visual detection). For quantitative PAH determination, the assay can be performed using a plate reader, in a spectrophotometer, or in a flow cell. For example, the color change can be determined by detecting a change in the specific absorbance of ultraviolet or visible light by the composition. In some embodiments, the color change can be determined by detecting a change in the specific absorbance at wavelengths of between about 360 nm to about 550 nm.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Recombinant Napthalene Dioxygenase

Naphthalene dioxygenase (NDO) was expressed in the *E. coli* strain JM109 (DE3) (PDTG141). This strain harbors a plasmid which can produce all four subunits of the enzyme. These cells were grown in RI medium with 0.1 mM thiamine, 25 mg/l ampicillin at 30° C. and 300 rpm until reaching an OD of 0.5 at 600 nm. Cultures were induced with a final concentration of 0.1 mM IPTG and 0.0003% $NH_4FeSO_4$ and shaken at 30° C.

NDO cultures were harvested 4 hours after induction with IPTG. Cultures were decanted into spin tubes and centrifuged for 15 minutes at 4500 rpm and 4° C. After centrifugation the media was decanted from the cells and the cell pellets were frozen at −20° C. overnight.

Frozen cell pellets were thawed on ice and resuspended in lysis buffer (50 mM Tris-Cl pH 7, 5% glycerol, 1 mM dithiothreitol and 0.2 mg/ml lysozyme) at a ratio of 1:20 (lysis buffer:culture volume) and allowed to lyse on ice for 1 hour. Two microliters of benzonase nuclease was added to reduce sample viscosity while incubating on ice for one hour. Lysed cells were then spun at 14,000 rpm for 30 minutes at 4° C. to separate soluble and insoluble fractions. Soluble lysates containing active NDO were decanted from the insoluble pellet fraction.

The soluble fraction was immediately dialyzed against a total of 4 L of cold dialysis buffer (50 mM Tris-Cl pH 7, 5% glycerol, 2 mM dithiothreitol) over the course of 24 hours in MWCO 3500 pore size dialysis tubing.

Example 2

Production of Recombinant NahB and NahC Enzymes

Figure 3:
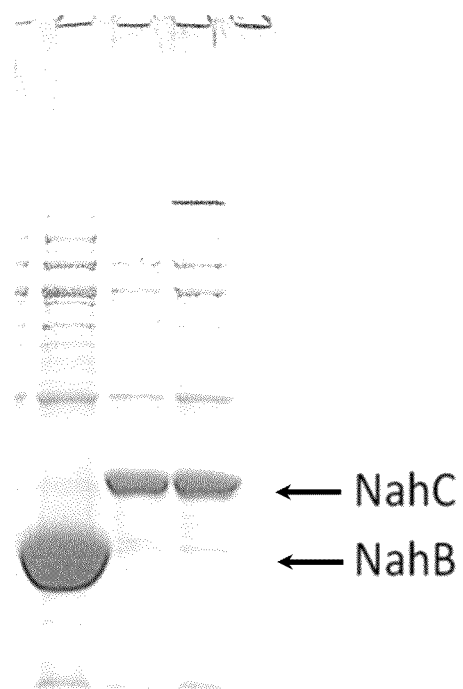
FIG. 3 depicts an electrophoresis gel of purified, desalted recombinant active NahB and NahC enzymes produced in *E. coli*.

Expression plasmids containing the genes encoding the NahB and NahC enzymes were transformed into *E. coli* BL21 Star (DE3). These transformations were used to induce overnight serial dilutions at 37 C. The log phase cultures from the serial dilution were used to inoculate 37° C. growth cultures in Rich Induction medium (20 g/l tryptone, 10 g/l yeast extract, 5 g/l NaCl). These cultures were induced at OD 1 using 1 mM IPTG; the cultures were induced at 18° C. for 18 hours. Cultures were decanted into spin tubes and centrifuged for 15 min at 4500 rpm and 4° C. After centrifugation cell pellets were immediately lysed with NahB (20 mM $KH_2PO_4$ pH 7.2, 1 mM dithiothreitol, 0.4% Triton X-100) or NahC (20 mM $KH_2PO_4$ pH 6.2, 1 mM dithiothreitol, 0.4% Triton X-100) lysis buffer respectively at a ratio of 1:20 (lysis buffer: culture volume). One microliter of benzonase was added to each sample to reduce viscosity; the samples were centrifuged at 14,000×g at 4° C. for 15 minutes to separate soluble and insoluble cell fractions. The soluble lysate fractions were aliquoted and frozen at −20° C. To enhance the stability of the enzymes, the NahB and NahC proteins were thawed and desalted using PD-10 columns equilibrated with 20 mM TrisCl pH 8.5. This purification step also reduced the level of background signal in the assay. FIG. 3 depicts an electrophoresis gel of purified, desalted recombinant active NahB and NahC enzymes produced in *E. coli*.

Example 3

Figure 4:
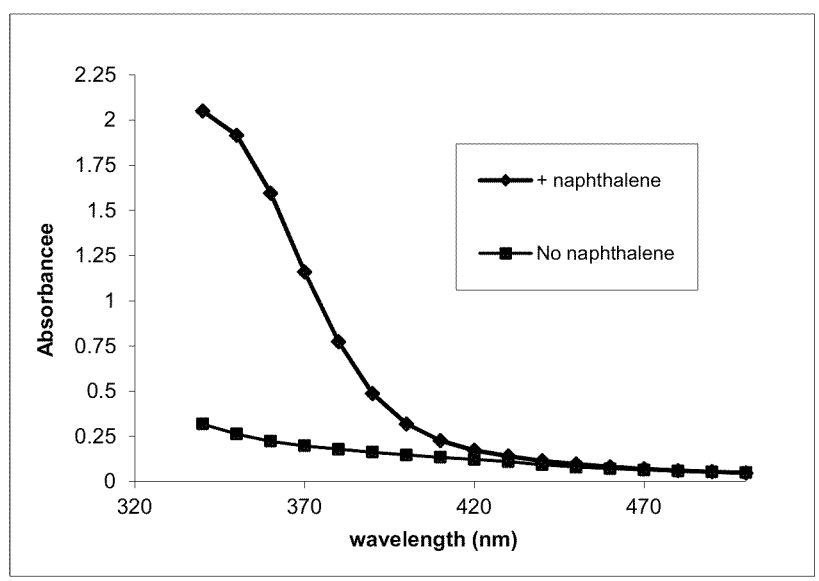
FIG. 4 depicts a spectrophotometric graph showing the absorbance caused by the presence of naphthalene placed is a NDO/NahB/NahC assay.

Colorimetric Detection of Naphthalene Using a Coupled Naphthalene Dioxygenase/NahB/NahC Assay 2 tubes each of NahB, Nahc, and NDO enzymes (1.7 ml aliquotes) were thawed from −20 C along with 2.6 mM NADH in water. 2.5 ml each of the NahC and NahB enzymes were desalted using PD-10 gel filtration and buffer exchanged into 20 mM Tris-Cl pH 8.5 at the same time. Once all of the reagents were thawed and desalted, positive and negative naphthalene reaction were made containing 127 ul each of NahB, NahC, and NDO with 20 ppm naphthalene in dimethylformamide (negative reactions contained only equal amounts dimethylformamide) and 0.133 mM NADH final concentration with a final reaction volume of 405 ul. The reaction was run at 25° C. for 2 hours and the sample absorbance was measured using a BioTek Synergy2 plate reader in the 320-640 nm wavelength range. The reaction containing naphthalene had significantly higher absorbance at 370 nm than the negative control reaction. Reactions for all PAH's conducted in the same, or a very similar format, depending on the volume of sample in the reaction. FIG. 4 depicts a spectrophotometric graph showing the absorbance caused by the presence of naphthalene placed in the above NDO/NahB/NahC assay.

Example 4

Colorimetric Detection of Fluorene in Clam Samples

Figure 5:
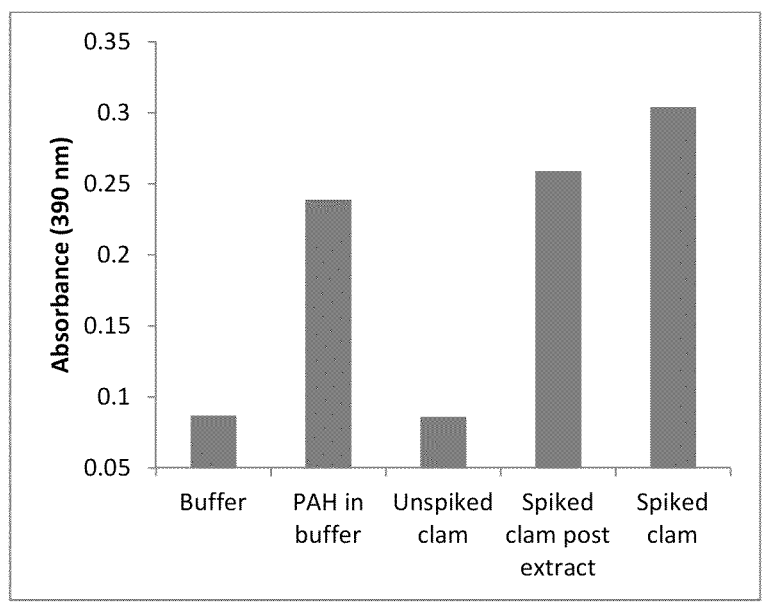
FIG. 5 depicts the absorbance of fluorene spiked clam samples in a NDO/NahB/NahC assay.

Approximately 25 g of clams were homogenized using a blender; a 2 g sample of this 25 g preparation was spiked to 80 ppm fluorene. This spiked 2 g sample of homogenized clam was place in a separatory funnel and 35 ml of dichloromethane was applied. The sample was vigorously mixed for 5 minutes and allowed to settle for an additional 5 minutes, the organic layer was then drained from the separatory funnel into a 250 ml round bottom flask. This process was repeated twice more for a total dichloromethane extraction volume of 105 ml. The extract was rotary evaporated down to ~5 ml using vacuum pressure and a 40° C. water bath and then transferred to a smaller 25 ml round bottom flask. The sample was then evaporated to dryness and resuspended in 800 μl of DMF for a 200 ppm solution. 10 μl of this 200 ppm solution was used in a 411 μl reaction as described in example 3. The reaction was run for 2 hr at 25° C. and then read on a BioTek Synergy2 plate reader from 320-640 nm. FIG. 5 depicts the absorbance of fluorene spiked clam samples in the NDO/NahB/NahC assay. Results indicated good recovery of fluorene from the extraction with a slightly higher absorbance than either the buffer control or the post-extraction spike at 390 nm.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of detecting the presence of polycyclic aromatic hydrocarbons comprising:

adding a sample suspected of containing one or more polycyclic aromatic hydrocarbons to a detection composition, wherein the detection composition comprises: NADH;

naphthalene dioxygenase; naphthalene 1,2-dihydroxy-1,2-dihydronaphthalene dehydrogenase; and 1,2-dihydroxynaphthalene dioxygenase; and detecting the presence of polycyclic aromatic hydrocarbons by determining if the color of the detection composition has changed due to the presence of polycyclic aromatic hydrocarbons.

2. The method of claim 1, wherein the sample is derived from food.

3. The method of claim 1, wherein the sample is obtained from an environment.

4. The method of claim 1, wherein the naphthalene dioxygenase is stabilized naphthalene dioxygenase.

5. The method of claim 4, wherein the stabilized naphthalene dioxygenase is produced by the method comprising:
obtaining naphthalene dioxygenase from a bacterial source; and
dialyzing the obtained naphthalene dioxygenase using dialysis tubing having a molecular weight cut off (MWCO) of less than or equal to about 7500.

6. The method of claim 5, wherein the dialysis is performed in the presence of dithiothreitol (DTT) and/or glycerol.

7. The method of claim 1, wherein the naphthalene 1,2-dihydroxy-1,2-dihydronaphthalene dehydrogenase is desalted before use in the detection composition.

8. The method of claim 1, wherein the 1,2-dihydroxynaphthalene dioxygenase is desalted before use in the detection composition.

9. The method of claim 1, wherein a change in the color of the detection composition is determined by detecting a change in the specific absorbance of ultraviolet or visible light by the detection composition.

10. The method of claim 1, wherein a change in the color of the detection composition is determined by detecting a change in the specific absorbance at wavelengths of between about 360 nm to about 550 nm.

\* \* \* \* \*